(12) United States Patent
Chang (10) Patent No.: US 10,314,872 B2
(45) Date of Patent: Jun. 11, 2019

(54) TUMOR CELL-INHIBITING COMPOSITION

(71) Applicant: Mei-Lin Chang, Taipei (TW)

(72) Inventor: Mei-Lin Chang, Taipei (TW)

( * ) Notice: Subject to any disclaimer, the term of this patent is extended or adjusted under 35 U.S.C. 154(b) by 501 days.

(21) Appl. No.: 14/971,893

(22) Filed: Dec. 16, 2015

(65) Prior Publication Data

US 2017/0173094 A1 Jun. 22, 2017

(51) Int. Cl.
| | | |
|---|---|---|
| *A61K 36/14* | (2006.01) | |
| *A61K 36/48* | (2006.01) | |
| *A61K 36/54* | (2006.01) | |
| *A61K 36/61* | (2006.01) | |
| *A61K 36/899* | (2006.01) | |

(52) U.S. Cl.
CPC .............. *A61K 36/14* (2013.01); *A61K 36/48* (2013.01); *A61K 36/54* (2013.01); *A61K 36/61* (2013.01); *A61K 36/899* (2013.01)

(58) Field of Classification Search
None
See application file for complete search history.

(56) References Cited

PUBLICATIONS

Li (PLOS One (Aug. 2014) vol. 9, No. 8, e104203).*

* cited by examiner

*Primary Examiner* — Susan Hoffman
(74) *Attorney, Agent, or Firm* — Chung-Ming Shih (57) ABSTRACT

A composition utilizing natural materials is selected from a group of plant extract comprising: Taiwan cypress, stout camphor tree, Taiwan incense cedar, *Cinnamomum camphora, Cymbopogon nardus, Litsea cubeba, Cinnamomum zeylanicum*, Taiwan *Cunninghamia lanceolatavar, Melaleuca alternifolia, Eucalyptus robusta* smith, *Cryptomeria japonica* and *Acacia confuse*. The tumor cell-inhibited composition having the efficiency of inhibiting the growth of tumor cells is formed by mixing these extracts based on a specific ratio.

5 Claims, 8 Drawing Sheets

TUMOR CELL-INHIBITING COMPOSITION

TECHNICAL FIELD

The present invention relates to a composition plant extract from a plant raw material based on a specific ratio. The composition has the efficiency of inhibiting the growth of tumor cells.

PRIOR ART

In the recent ten years, cancer ranks number one among the top ten causes of death, in which the lung cancer, hepatic carcinoma and intestinal cancer rank top three from both of male and female aspects. From female aspect, the fourth and fifth mortalities are breast cancer and pancreatic cancer, and from male aspect, the fourth and fifth ones are oral cancer and esophageal cancer. All of the domestic and overseas doctors and research scholars are devoted to the research of avoiding or reducing the generation or proliferation of tumor cell.

Pulmonary fibrosis refers to the pulmonary alveoli is being replaced by fibrous matter due to the effect of the pulmonary issue being subjected to phlogosis, so that the soft pulmonary issue becomes hard and loses its elasticity, gradually, the lungs would lose the ability of contraction, relaxation, and gas exchange. The patients would have the symptoms of brachypnea, chest tightness or dry cough, etc., severely, may not breathe and cause respiratory failure eventually.

Nowadays, the aforementioned diseases all have medicine and method to carry out a treatment or an inhibition. However, these medicines mostly are chemical-synthesized or radiotherapy, hence, during the treatment, many patients would have side effects, and the side effects would make the patients much more uncomfortable comparing to the illness from the diseases. This is a huge deficiency.

Taiwan cypress (*Chamaecyparis formosensis*) is one of the evergreen arbors in *Conifers Cupressaceae*, it is an important species among the needle-leaved trees. Taiwan cypress has some characteristics such as a scent without pungent smell, the wooden quality of hardness, the abilities not to be rotten or damaged by worms. Furthermore, the researches indicate that Taiwan cypress has the superior inhibitory function to typhoid, *Escherichia coli*, Achorion and *Staphylococcus auresus*, and Taiwan cypress also has an anti-inflammatory function.

Stout camphor tree (*Cinnamomum micranthun*) belongs to Lauraceous plants. Its appearance is tall, straight and delicate, hence, it is a perfect species for landscape design. Its wooden quality is superior and has a unique scent, which would also be the excellent material for wooden art craft and furniture. Stout camphor tree contains triterpenoids, superoxide dismutase, adenoside, polysaccharide, multiple proteins, and multiple vitamins, etc. It has the functions of anti-tumor, enhancing the immunity, reducing blood sugar and cholesterol and the like. Most of the related researches about the anti-cancer focus on the stout camphor tree. There is no research revealing that the stout camphor tree itself or its extract has specific function of anti-tumor.

Taiwan incense cedar (*Calocedrus formosana*) belongs to a Taiwan specific species, an evergreen big arbor of *Cupressaceae* Taiwan incense cedar. It has special scent, and its texture is compact and delicate. The research discloses that its extracts have the activities of anti-fungus, anti-oxidation and anti-inflammation. However, the researches related to the components of Taiwan incense cedar mainly are the extracts from branches and leaves, and less is about the extracts from wooden core. There is no research revealing that the extract of the Taiwan incense cedar has specific function of anti-cancer.

The recent researches discover that many plants (as aforementioned) have the functions of anti-inflammation or anti-oxidation, especially the distilled extracts of the plants would have the function to improve the cell membrane permeability for the nutrition and the oxygen needed by the cells getting into the cells and exhausting the waste produced by the cells out of the cells, so that the cell metabolism can be enhanced. Therefore, the cell may healthily be activated, and all the tissues, organs and immune system may function normally to provide human body the immunity, resistance and the ability of self-healing.

Prior art disclosed a method for preparing a plant extract liquid and its composition solution, wherein comprises shaving the plant raw material into pieces, and then putting the pieces in the main furnace of a steam kiln, and lighting up the wood to have the fractional distillation temperature to be set up. When each of the plant raw materials reach its steam reaction time, the steam extracts of each plants can be obtained via cooling and separation. The extract made by utilizing the method in prior art, no matter the oil layer or the water layer (purification), is different from the oil and the purification made by a distillation method carried out by a regular machine, which is characterized in that the extracts (oil or purification) made by the method would contain much richer compound from the distillation method carried out by the regular machine.

In addition, although these plants have the functions of anti-oxidation, anti-inflammation and the like individually, the recent researches know nothing about what treatment for diseases that a single plant can provide. Furthermore, a single plant offers a poor efficiency on the tumor inhibition and cannot be widely applied. These are the two deficiencies.

The applicants were aware of the deficiency of inhibition techniques, so that they invented a way to inhibit, reduce or ease the symptoms of the disease utilizing composite natural materials for improving the aforementioned conventional deficiency.

SUMMARY OF THE INVENTION

The main purpose of the present invention is providing a composition of natural plant extract (TGLON composition). The composition has the function of adjusting or facilitating the cell metabolism, and has the function of inhibiting the growth of tumor cells.

For achieving the aforementioned purpose, the characteristic of the present invention is utilizing the theory of mixing the plants grown from low, middle and high altitudes in Taiwan to design the composition of The Greatest Love of Nature composite plant extract (TGLON composition). Utilizing the following plant extracts with the specific ratio to combine a tumor cell-inhibited composition, wherein its components comprise: Taiwan cypress, stout camphor tree, Taiwan incense cedar, *Cinnamomum camphora*, *Cymbopogon nardus*, *Litsea cubeba*, *Cinnamomum zeylanicum*, Taiwan *Cunninghamia lanceolatavar*, *Melaleuca alternifolia*, *Eucalyptus robusta* smith, *Cryptomeria japonica* and *Acacia confuse* extracts.

The other characteristic of the present invention is the disclosed plant extract is the purification made by utilizing the method of prior art. The characteristic of the purification made by utilizing the method in prior art is having richer compound components comparing to a regular purification.

After a serial dilution of the TGLON composition, incubating the breast cancer cells (MCF-7), hepatic carcinoma cells (HepG2) and lung fibrous cells (MRC-5) for 72 hours, and then utilizing ELISA Reader (540 nm) to analyze the survival rate of these cell strains. As a result, when the composition is diluted by 40 folds, it has the inhibitory efficiency of cell growth above 50%.

EMBODIMENT

For a better knowing and understanding of the tumor cell-inhibited composition of the present invention at the examiner's convenience, the present invention is illustrated in details by the examples with figures hereafter.

One of the tumor cell-inhibited composition (TGLON composition) of the present invention comprising the plant extract selected from the following group: Taiwan cypress, stout camphor tree, Taiwan incense cedar, *Cinnamomum camphora*, *Cymbopogon nardus*, *Litsea cubeba*, *Cinnamomum zeylanicum*, Taiwan *Cunninghamia lanceolatavar*, *Melaleuca alternifolia*, *Eucalyptus robusta* smith, *Cryptomeria japonica* and *Acacia confuse*. The present invention utilized the separation techniques to extract the effective component from the plant raw material, wherein the separation techniques are: distillation method, solvent extraction method, cold pressed method, supercritical carbon dioxide extraction and absorption method, etc. The TGLON composition itself has the function of adjusting or facilitating the cell metabolism, and has the function of inhibiting the growth of tumor cells.

For further illustrations, the plant extract of the present invention is the purification made by distillation method. For another further illustration, the purification is the purification made by the method disclosed in prior art, which is characterized in having richer compound components comparing to a regular purification.

The present invention also utilized the theory of mixing the plants grown from low, middle and high altitudes in Taiwan to be provided with a full efficiency in treatment, and further have the purification of the aforementioned plants mixed to become the tumor cell-inhibited composition. The weight percentage of the mixed composition is: 40%-50% of the Taiwan cypress purification, 10%-20% of the stout camphor tree purification, 10%-20% of the Taiwan incense cedar purification, 8%-10% of the *Cinnamomum camphora* purification, 8%-10% of the *Cymbopogon nardus* purification, 6%-8% of the *Litsea cubeba* purification, 6%-8% of the *Cinnamomum zeylanicum* purification, 4%-6% of the Taiwan *Cunninghamia lanceolatavar* purification, 2%-4% of the *Melaleuca alternifolia* purification, 2%-4% of the *Eucalyptus robusta* smith purification, 2%-4% of the *Cryptomeria japonica* purification and 2%-4% of the *Acacia confuse* purification.

Furthermore, utilizing the tumor cell-inhibited composition to carry out the survival experiments to the tumor cells based on the breast cancer cells (MCF-7), lung fibrous cells (MIRC-5) and hepatic carcinoma cell (HepG2).

Example 1

In the present example, the tumor cell-inhibited compositions are diluted by different multiples, and then are added into breast cancer cell strain (MCF-7) to be cultured. Furthermore, utilizing MTT colormetric method to test the composition inhibiting the growth of the breast cancer cell strain. The applicants observed whether the composition has the inhibitory efficiency to the growth of the breast cancer cell strain and its inhibitory concentration.

Firstly, culture the well-growing breast cancer cell strain into 96-well microplate, about 3,000 cells per well, then put the plate into the 5% of $CO_2$, 37□ incubator overnight, then add the tumor cell-inhibited composition. Before adding the composition, filter the composition by 0.22 μm filter to remove of bacteria. Then serial dilute the composition by distill water with two folds, completely shock the diluted composition into 96-well microplate, and the final concentration would be 40960×, 20480×, 10240×, 5120×, 2560×, 1280×, 640×, 320×, 160×, 80×, 40×, 20× and 10×. Incubating them in the 5% of $CO_2$, 37° C. incubator for 72 hours, after 72 hours adding 1/10 of the total volume of MTT (5 mg/mL) solution into each well. Incubating them in the 5% of $CO_2$, 37° C. incubator for 4 hours, and then remove the mixed liquid in each well. Adding 100 μl DMSO into each well to dissolve blue-purple crystal (formazan) in the cells, and furthermore place the 96-well microplate in the ELISA reader to read and analyze the data.

Figure 1:
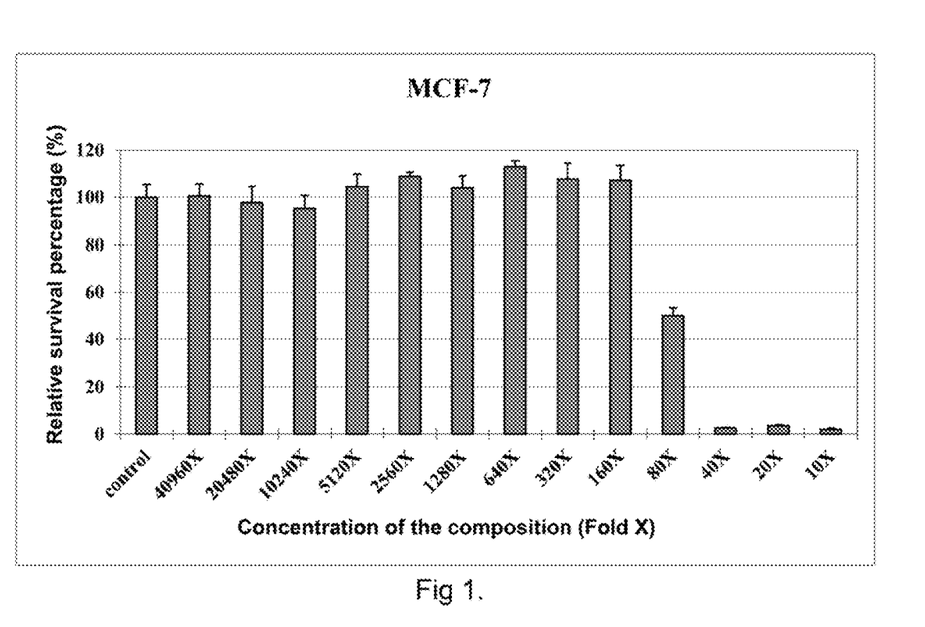
FIG. 1 is the diagram disclosing the relative survival percentage of the composition of the present invention to the breast cancer cell strain.
Figure 2:
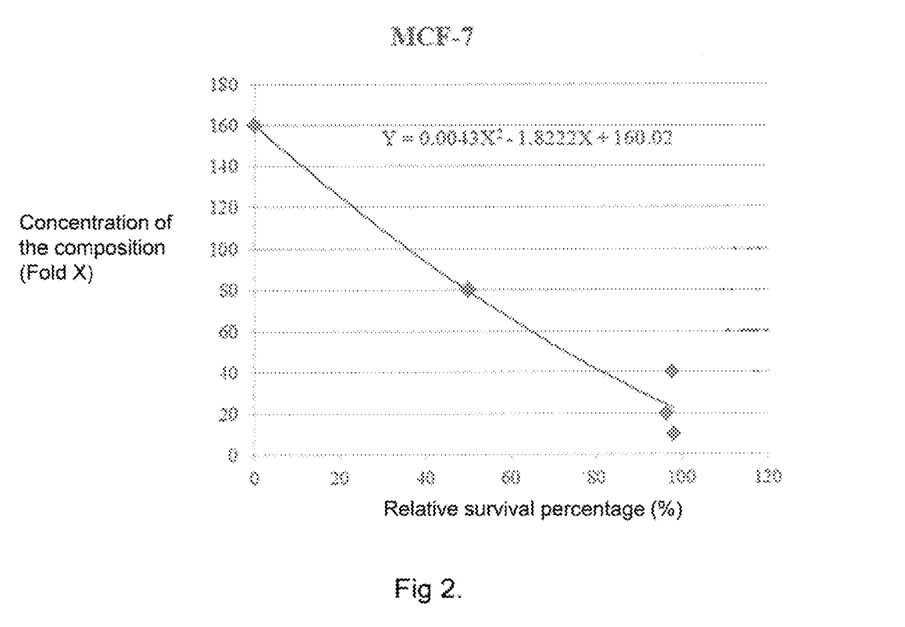
FIG. 2 is the diagram disclosing the relative inhibitory percentage of the composition of the present invention to the breast cancer cell strain.

Please referring to Table 1 and FIGS. 1 and 2, the composition has the significant inhibitory efficiency to the growth of the breast cancer cell. When the dilution multiple is 80 folds, its inhibitory efficiency may achieve to 50% and more. When the dilution multiple is 10 folds to 40 folds, the inhibitory efficiency composition to the breast cancer cells may achieve to 98% and more.

Please further referring to FIG. 2, based on the data of the concentration of the composition (Y axis) and its corresponding inhibitory percentage (X axis), analyzing the two-dimensional linear regression and we may obtain a regression formula: $Y=160.02-1.8222X+0.0043X^2$. If X=50 in this regression formula and we can get that Y=80, the value means the semi-inhibition concentration (50% Inhibition Concentration, $IC_{50}$) of the composition to the breast cancer cell strain with 80 folds of diluted concentration.

the inhibitory efficiency to the growth of the lung fibrous cell strain and its inhibitory concentration.

Firstly, culture the well-growing lung fibrous cell strain into 96-well microplate, about 3,000 cells per well, then put the plate into the 5% of $CO_2$, 37° C. incubator overnight, then add the tumor cell-inhibited composition. Before adding the composition, filter the composition by 0.22 μm filter to remove of bacteria. Then serial dilute the composition by distill water with two folds, completely shock the diluted composition into 96-well microplate, and the final concentration would be 40960×, 20480×, 10240×, 5120×, 2560×, 1280×, 640×, 320×, 160×, 80×, 40×, 20× and 10×. Incubating them in the 5% of $CO_2$, 37° C. incubator for 72 hours, after 72 hours adding 1/10 of the total volume of MTT (5 mg/mL) solution into each well. Incubating them in the 5% of $CO_2$, 37° C. incubator for 4 hours, and then remove the mixed liquid in each well. Adding 100 μl DMSO into each well to dissolve blue-purple crystal (formazan) in the cells, and furthermore place the 96-well microplate in the ELISA reader to read and analyze the data.

Figure 3:
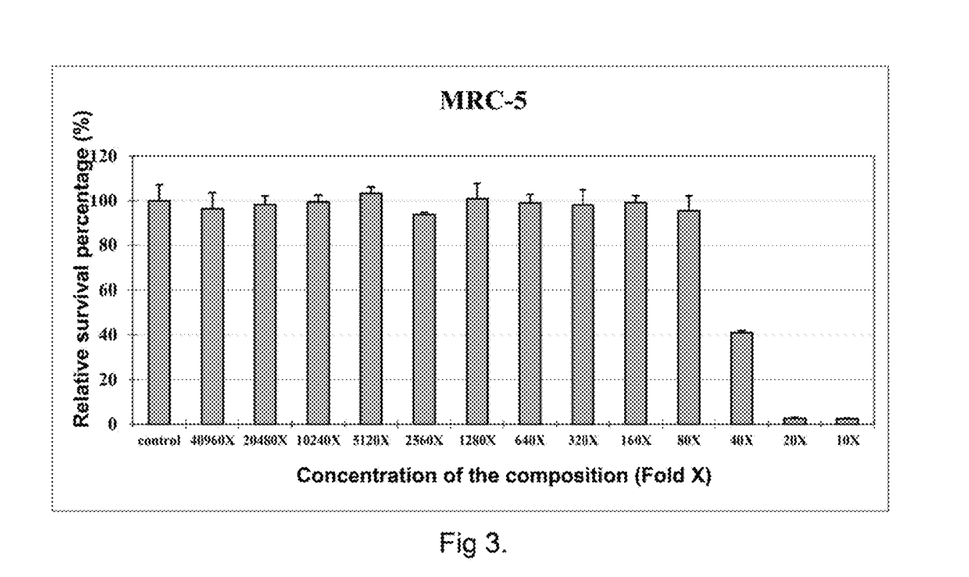
FIG. 3 is the diagram disclosing the relative survival percentage of the composition of the present invention to the lung fibrous cell strain.
Figure 4:
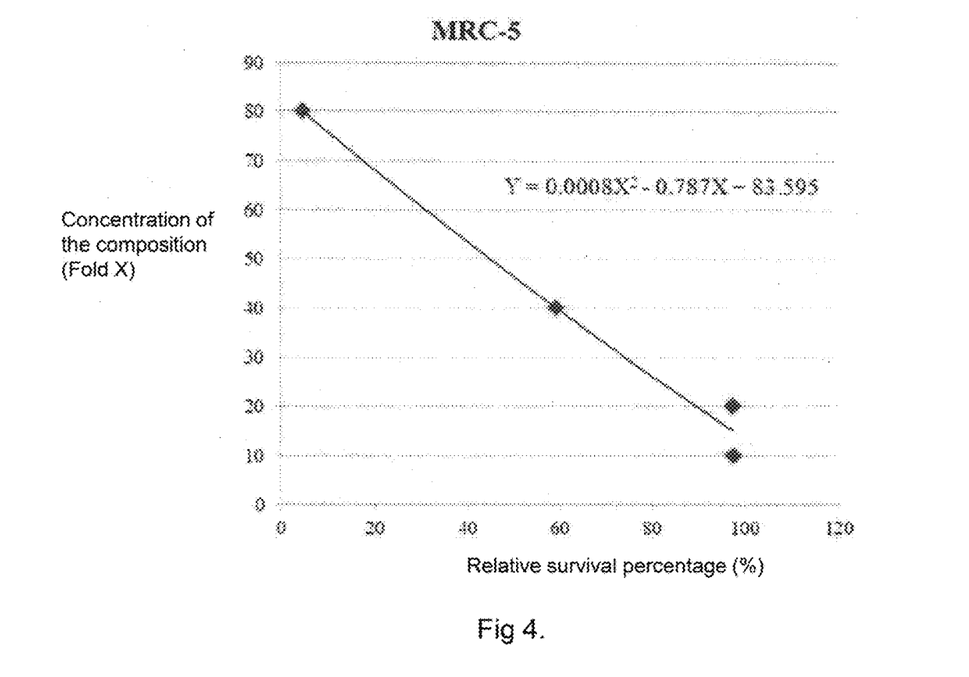
FIG. 4 is the linear regression curve diagram disclosing the inhibitory percentage of the composition of the present invention to the lung fibrous cell strain.

Please referring to Table 2 and FIGS. 3 and 4, the composition has the significant inhibitory efficiency to the growth of the lung fibrous cell. When the dilution multiple is 80 folds, its inhibitory efficiency may achieve to 50% and more. When the dilution multiple is 10 folds to 40 folds, the inhibitory efficiency composition to the lung fibrous cells may achieve to 97% and more.

Please further referring to FIG. 4, based on the data of the concentration of the composition (Y axis) and its corresponding inhibitory percentage (X axis), analyzing the two-dimensional linear regression and we may obtain a regression formula: $Y=83.595-0.787X+0.0008X^2$. If X=50 in this regression formula and we can get that Y=46, the value means the semi-inhibition concentration (50% Inhibition Concentration, $IC_{50}$) of the composition to the breast cancer cell strain with 46 folds of diluted concentration.

TABLE 1

The growth inhibitory test of the composition of the present invention to the breast cancer cell strain (MCF-7)

| Concentration of the composition (Fold X) | O.D. value (mean ± SD) | Relative survival percentage (%) (mean ± SD) | Relative inhibitory percentage (%) |
|---|---|---|---|
| Control | 1.188 ± 0.065 | 100.0 ± 5.5 | 0 |
| 40960X | 1.195 ± 0.062 | 100.5 ± 5.3 | 0 |
| 20480X | 1.162 ± 0.082 | 97.7 ± 6.9 | 2.3 |
| 10240X | 1.134 ± 0.064 | 95.4 ± 5.4 | 4.6 |
| 5120X | 1.242 ± 0.064 | 104.5 ± 5.4 | 0 |
| 2560X | 1.295 ± 0.021 | 108.9 ± 1.8 | 0 |
| 1280X | 1.234 ± 0.063 | 103.9 ± 5.3 | 0 |
| 640X | 1.342 ± 0.030 | 113.0 ± 2.5 | 0 |
| 320X | 1.283 ± 0.079 | 107.9 ± 6.6 | 0 |
| 160X | 1.275 ± 0.074 | 107.3 ± 6.2 | 0 |
| 80X | 0.579 ± 0.039 | 50.2 ± 3.3 | 49.8 |
| 40X | 0.027 ± 0.004 | 2.3 ± 0.3 | 97.7 |
| 20X | 0.043 ± 0.004 | 3.6 ± 0.3 | 96.4 |
| 10X | 0.024 ± 0.005 | 2.0 ± 0.4 | 98.0 |

TABLE 2

The growth inhibitory test of the composition of the present invention to lung fibrous cell strain (MRC-5)

| Concentration of the composition (Fold X) | O.D. value (mean ± SD) | Relative survival percentage (%) (mean ± SD) | Relative inhibitory percentage (%) |
|---|---|---|---|
| Control | 1.177 ± 0.084 | 100.0 ± 7.1 | 0 |
| 40960X | 1.134 ± 0.088 | 96.3 ± 7.5 | 3.7 |
| 20480X | 1.157 ± 0.046 | 98.3 ± 3.9 | 1.7 |
| 10240X | 1.171 ± 0.037 | 99.5 ± 3.1 | 0.5 |
| 5120X | 1.216 ± 0.034 | 103.3 ± 2.9 | 0 |
| 2560X | 1.104 ± 0.011 | 93.8 ± 0.9 | 6.2 |
| 1280X | 1.189 ± 0.078 | 101.0 ± 6.7 | 0 |
| 640X | 1.167 ± 0.046 | 99.1 ± 3.9 | 0.9 |
| 320X | 1.153 ± 0.082 | 98.0 ± 7.0 | 2 |
| 160X | 1.168 ± 0.036 | 99.2 ± 3.1 | 0.7 |
| 80X | 1.124 ± 0.081 | 95.4 ± 6.9 | 4.6 |
| 40X | 0.482 ± 0.012 | 40.9 ± 1.0 | 59.1 |
| 20X | 0.032 ± 0.004 | 2.7 ± 0.3 | 97.3 |
| 10X | 0.030 ± 0.004 | 2.5 ± 0.3 | 97.5 |

Example 2

In the present example, the tumor cell-inhibited compositions are diluted by different multiples, and then are added into lung fibrous cell strain (MRC-5) to be cultured. Furthermore, utilizing MTT colormetric method to test the composition inhibiting the growth of the lung fibrous cell strain. The applicants observed whether the composition has Example 3

In the present example, the tumor cell-inhibited compositions are diluted by different multiples, and then are added into hepatic carcinoma cell strain (HepG2) to be cultured. Furthermore, utilizing MTT colormetric method to test the composition inhibiting the growth of the hepatic carcinoma cell strain. The applicants observed whether the composition has the inhibitory efficiency to the growth of the lung hepatic carcinoma cell strain and its inhibitory concentration.

Firstly, culture the well-growing hepatic carcinoma cell strain into 96-well microplate, about 3,000 cells per well, then put the plate into the 5% of $CO_2$, 37° C. incubator overnight, then add the tumor cell-inhibited composition. Before adding the composition, filter the composition by 0.22 μm filter to remove of bacteria. Then serial dilute the composition by distill water with two folds, completely shock the diluted composition into 96-well microplate, and the final concentration would be 40960×, 20480×, 10240×, 5120×, 2560×, 1280×, 640×, 320×, 160×, 80×, 40×, 20× and 10×. Incubating them in the 5% of $CO_2$, 37° C. incubator for 72 hours, after 72 hours adding 1/10 of the total volume of MTT (5 mg/mL) solution into each well. Incubating them in the 5% of $CO_2$, 37° C. incubator for 4 hours, and then remove the mixed liquid in each well. Adding 100 μl DMSO into each well to dissolve blue-purple crystal (formazan) in the cells, and furthermore place the 96-well microplate in the ELISA reader to read and analyze the data.

Figure 5:
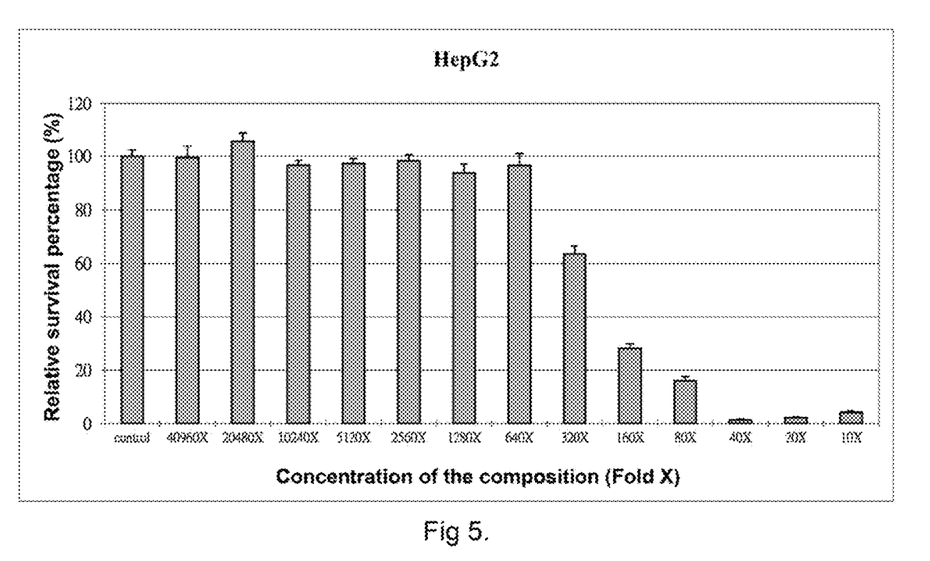
FIG. 5 is the diagram disclosing the relative survival percentage of the composition of the present invention to the hepatic carcinoma cell strain.
Figure 6:
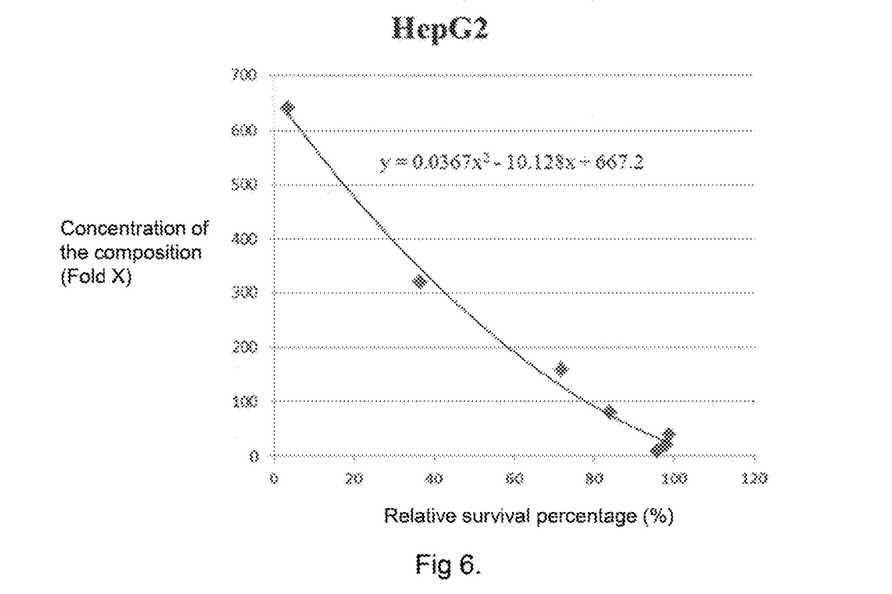
FIG. 6 is the linear regression curve diagram disclosing the inhibitory percentage of the composition of the present invention to the hepatic carcinoma cell strain.

Please referring to Table 3 and FIGS. 5 and 6, the composition has the significant inhibitory efficiency to the growth of the hepatic carcinoma cell. When the dilution multiple is 160 folds, its inhibitory efficiency may achieve to 50% and more. When the dilution multiple is 10 folds to 40 folds, the inhibitory efficiency composition to the lung fibrous cells may achieve to 97% and more.

Please further referring to FIG. 6, based on the data of the concentration of the composition (Y axis) and its corresponding inhibitory percentage (X axis), analyzing the two-dimensional linear regression and we may obtain a regression formula: $Y=0.0367X^2-10.128X+66.72$. If $X=50$ in this regression formula and we can get that $Y=253$, the value means the semi-inhibition concentration (50% Inhibition Concentration, $IC_{50}$) of the composition to the hepatic carcinoma cell strain with 253 folds of diluted concentration.

TABLE 3

The growth inhibitory test of the composition of the present invention to the hepatic carcinoma cell strain (HepG2)

| Concentration of the composition (Fold X) | O.D. value (mean ± SD) | Relative survival percentage (%) (mean ± SD) | Relative inhibitory percentage (%) |
|---|---|---|---|
| Control | 1.206 ± 0.027 | 100.0 ± 2.3 | — |
| 40960X | 1.199 ± 0.055 | 99.4 ± 4.6 | 0.6 |
| 20480X | 1.276 ± 0.037 | 105.8 ± 3.1 | — |
| 10240X | 1.164 ± 0.023 | 96.5 ± 1.9 | 3.5 |
| 5120X | 1.173 ± 0.023 | 97.2 ± 1.9 | 2.8 |
| 2560X | 1.184 ± 0.028 | 98.2 ± 2.3 | 1.8 |
| 1280X | 1.131 ± 0.039 | 93.8 ± 3.2 | 6.2 |
| 640X | 1.163 ± 0.055 | 96.4 ± 4.5 | 3.6 |
| 320X | 0.767 ± 0.036 | 63.5 ± 3.0 | 36.5 |
| 160X | 0.342 ± 0.020 | 28.3 ± 1.7 | 71.7 |
| 80X | 0.194 ± 0.019 | 16.0 ± 1.6 | 84.0 |
| 40X | 0.017 ± 0.002 | 1.4 ± 0.2 | 98.6 |
| 20X | 0.026 ± 0.002 | 2.2 ± 0.2 | 97.8 |
| 10X | 0.051 ± 0.005 | 4.2 ± 0.4 | 95.8 |

Example 4

Figure 7:
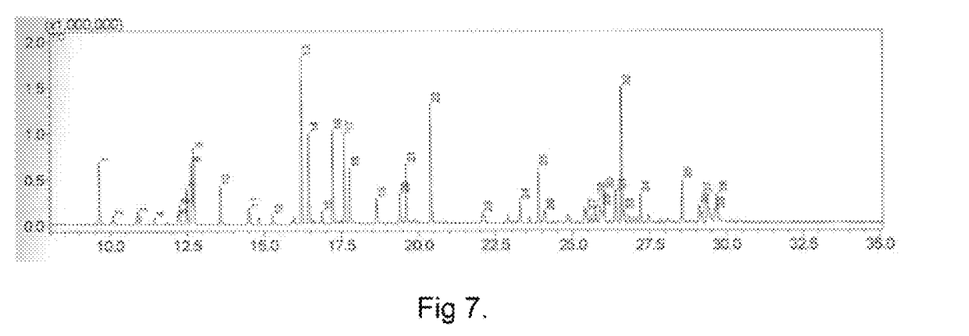
FIG. 7 is the analysis chart of the components of the composition of the present invention.

Please refers to Table 4 and FIG. 7, the composition can be confirmed that it has the function of inhibiting the growth of the tumor cells based on the aforementioned examples. Furthermore, the inventors have the tumor cell-inhibited composition analyzed by GC/MS, wherein the contained chemical components comprise: 1,8-Cineole, Camphor, Borneol, Terpinen-4-ol, α-Terpineol, (-)-Myrtenol, cis-Myrtanol, α-Pinene, Camphene, Sabinene, Myrcene, 1,4-Cineole, α-Terpinene, Cymene, Limonene, γ-Terpinene, α-Terinolen, α-Fenchol, Citronellal, Citronellol, Nerol, Safrole, α-Terpinyl acetate, β-Elemene, α-Cedrene, β-Cedrene, α-Amorphene, β-Selinene, γ-2-Cadinene, α-Muurolene, γ-Cadinene, δ-Cadinene, β-Cadinene, α-Elemol, Cedrol, α-Cubebene, γ-Eudesmol, β-Eudesmol, tau-Muurolol.

TABLE 4

| Peak | Compound name |
|---|---|
| 1 | α-Pinene |
| 2 | Camphene |
| 3 | Sabinene |
| 4 | Myrcene |
| 5 | 1,4-Cineole |
| 6 | α-Terpinene |
| 7 | Cymene |
| 8 | Limonene |
| 9 | 1,8-Cineole |
| 10 | γ-Terpinene |
| 11 | α-Terpinene |
| 12 | α-Fenchol |
| 13 | Camphor |
| 14 | Citronellal |
| 15 | Borneol |
| 16 | Terpinen-4-ol |
| 17 | α-Terpineol |
| 18 | (-)-Myrtenol |
| 19 | Citronellol |
| 20 | Nerol |
| 21 | cis-Myrtanol |
| 22 | Safrole |
| 23 | α-Terpinyl acetate |
| 24 | β-Elemene |
| 25 | α-Cedrene |
| 26 | β-Cedrene |
| 27 | α-Amorphene |
| 28 | β-Selinene |
| 29 | γ-2-Cadinene |
| 30 | α-Muurolene |
| 31 | γ-Cadinene |
| 32 | δ-Cadiene |
| 33 | β-Cedrene |
| 34 | α-Elemol |
| 35 | Cedrol |
| 36 | α-Cubebene |
| 37 | γ-Eudesmol |
| 38 | β-Eudesmol |
| 39 | tau-Muurolol |

Please referring to FIGS. 8 to 19 and Table 5 to 16, the inventors further utilize GC/MS to analyze the components of the tumor cell-inhibited composition in each plant individually. The component less than 0.05% is not being labelled in the figures.

Figure 8:
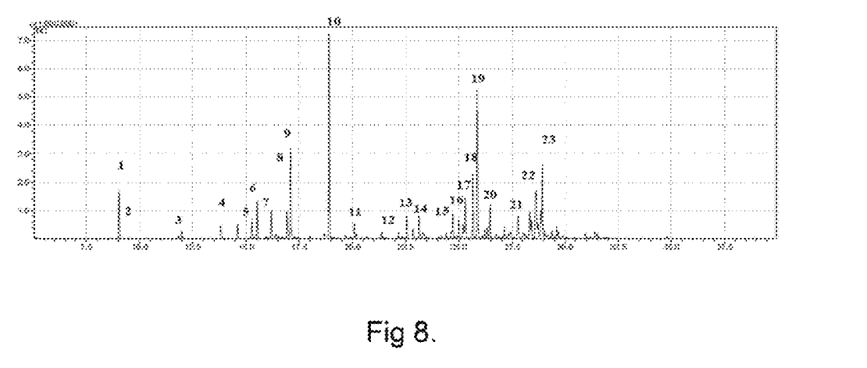
FIG. 8 is the analysis chart of the Taiwan cypress purification of the composition of the present invention.

Please refer to Table 5 and FIG. 8, for chemical components contained in Taiwan cypress.

TABLE 5

| Peak | Compound name | Chemical formula |
|---|---|---|
| 1 | α-Pinene | C10H16 |
| 2 | Camphene | C10H16 |
| 3 | Limonene | C10H16 |
| 4 | Terpinolene | C10H16 |
| 5 | (1R)-(+)-norinone | C9H14O |
| 6 | Camphor | C10H16O |
| 7 | Borneol | C10H18O |
| 8 | α-Terpineol | C10H18O |
| 9 | (-)-Myrtenol | C10H16O |
| 10 | Trans-Myrtanol | C10H18O |
| 11 | cis-terpin hydrate | C10H20O2 |

TABLE 5-continued

| Peak | Compound name | Chemical formula |
|---|---|---|
| 12 | α-Terpinyl acetate | C12H20O2 |
| 13 | α-Terpinyl formate | C11H18O2 |
| 14 | α-Cedrene | C15H24 |
| 15 | γ-Cadinene | C15H24 |
| 16 | β-Selinene | C15H24 |
| 17 | α-Muurolene | C15H24 |
| 18 | Cadinene | C15H24 |
| 19 | δ-Cadinene | C15H24 |
| 20 | α-Elemol | C15H26O |
| 21 | Cedrol | C15H26O |
| 22 | epi-α-Muurolene | C15H26O |
| 23 | α-Cadinol | C15H26O |

Figure 9:
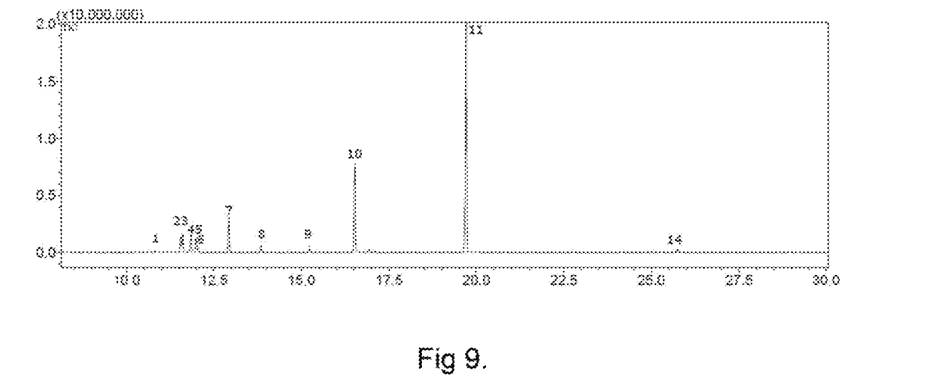
FIG. 9 is the analysis chart of the stout camphor tree purification of the composition of the present invention, wherein the component less than 0.05% is not being labelled.

Please refer to Table 6 and FIG. 9, for chemical components contained in stout camphor tree.

TABLE 6

| 1 | Myrcene | C10H16 |
|---|---|---|
| 2 | 1,4-Cineole | C10H18O |
| 3 | α-Terpinene | C10H16 |
| 4 | p-Cymene | C10H14 |
| 5 | Limonene | C10H16 |
| 6 | Cineole:Eucalyptol | C10H18O |
| 7 | γ-Terpinene | C10H16 |
| 8 | α-Terpinolene | C10H16 |
| 9 | 1-Terpineol | C10H16 |
| 10 | 4-Terpineol | C10H16 |
| 11 | Safrole | C10H10O2 |
| 12 | 3-Hydroxy-5-methyl-2-nitrocyclohexyl acetate | C9H15NO5 |
| 13 | Myristicin | C11H12O3 |
| 14 | δ-Cadinene | C15H24 |

Figure 10:
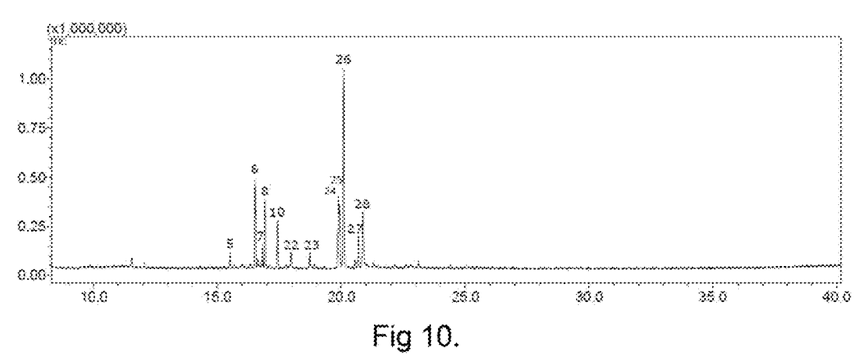
FIG. 10 is the analysis chart of the Taiwan incense cedar purification of the composition of the present invention, wherein the component less than 0.05% is not being labelled.

Please refer to Table 7 and FIG. 10, for chemical components contained in Taiwan incense cedar.

TABLE 7

| Peak | Compound name | Chemical formula |
|---|---|---|
| 1 | α-Pinene | C10H16 |
| 2 | α-Fenchene | C10H16 |
| 3 | p-Cymene | C10H14 |
| 4 | Limonene | C10H16 |
| 5 | Camphor | C10H16O |
| 6 | 4-Tepineol | C10H18O |
| 7 | Terpineol Isomer | C10H18O |
| 8 | α-Terpineol | C10H18O |
| 9 | (−)-Myrtenol | C10H16O |
| 10 | Verbenone | C10H14O |
| 11 | Trans-Myrtanol | C10H18O |
| 12 | Nopol* | C11H18O |
| 13 | β-Elemene | C15H24 |
| 14 | Myrtensaeure | C10H14O2 |
| 15 | α-Muurolene | C15H24 |
| 16 | γ-Cadinene | C15H24 |
| 17 | δ-Cadinene | C15H24 |
| 18 | α-Cadinol | C15H26O |
| 19 | 3(10)-Caren-4-ol. acetoacetic acid ester* | C14H20O3 |
| 20 | C12H20O2* | C12H20O2 |
| 21 | C12H20O2* | C12H20O2 |
| 22 | Oct-7-enol | C10H20O |
| 23 | Piperitone* | C10H16O |
| 24 | C10H20O2* | C10H20O2 |
| 25 | C10H20O2* | C10H20O2 |

TABLE 7-continued

| Peak | Compound name | Chemical formula |
|---|---|---|
| 26 | cis-terpin hydrate | C10H20O2 |
| 27 | C10H20O2* | C11H20O2 |
| 28 | C10H16* | C10H16O |

*similarity scores were less than 95% among data base.

Figure 11:
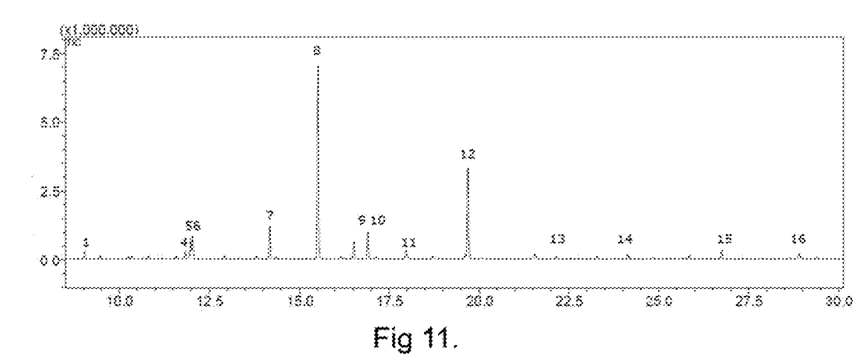
FIG. 11 is the analysis chart of the *Cinnamomum camphora* purification of the composition of the present invention, wherein the component less than 0.05% is not being labelled.

Please refer to Table 8 and FIG. 11, for chemical components contained in Cinnamomum camphora.

TABLE 8

| Peak | Compound name | Chemical formula |
|---|---|---|
| 1 | α-(+)-Pinene | C10H16 |
| 2 | Camphene | C10H16 |
| 3 | β-Pinene | C10H16 |
| 4 | p-cymene | C10H14 |
| 5 | Limonene | C10H16 |
| 6 | Cineole:Eucalyptol | C10H18O |
| 7 | Linalool | C10H18O |
| 8 | Camphor | C10H16O |
| 9 | 4-Terpineol | C10H18O |
| 10 | α-Terpineol | C10H18O |
| 11 | L-Citronellol | C10H20O |
| 12 | Safrole | C10H20O2 |
| 13 | α-Copaene | C15H24 |
| 14 | (E)-β-Farnesene | C15H24 |
| 15 | Nerolidol | C15H26O |
| 16 | (−)-Guaiol | C15H26O |

Figure 12:
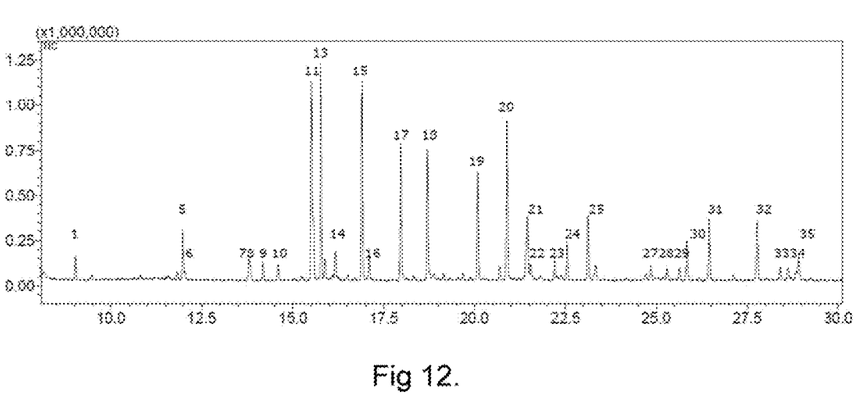
FIG. 12 is the analysis chart of the *Cymbopogon nardus* purification of the composition of the present invention, wherein the component less than 0.05% is not being labelled.

Please refer to Table 9 and FIG. 12, for chemical components contained in Cymbopogon nardus.

TABLE 9

| Peak | Compound name | Chemical formula |
|---|---|---|
| 1 | α-(+)-Pinene | C10H16 |
| 2 | Camphene | C10H16 |
| 3 | β-Myrcene | C10H16 |
| 4 | p-Cymene | C10H14 |
| 5 | Limonene | C10H16 |
| 6 | Cineole:Eucalyptol* | C10H18O |
| 7 | L-Fenchone | C10H16O |
| 8 | Terpinolene | C10H16 |
| 9 | Linalool | C10H18O |
| 10 | (+)-Fenchol | C10H18O |
| 11 | Camphor | C10H16O |
| 12 | (−)-Isopulegol* | C10H18O |
| 13 | β-Citronellal | C10H18O |
| 14 | Borneol | C10H18O |
| 15 | α-Terpineol | C10H18O |
| 16 | γ-Terpineol | C10H18O |
| 17 | L-Citronellol | C10H20O |
| 18 | β-Geraniol | C10H18O |
| 19 | Terpin Hydrate | C10H20O2 |
| 20 | para-menthane-3,8-diol | C10H20O2 |
| 21 | Citronellyl acetate | C12H22O2 |
| 22 | Eugenol | C10H12O3 |
| 23 | Geranyl acetate | C15H24 |
| 24 | β-Elemene | C15H24 |
| 25 | α-Cedrene | C15H24 |
| 26 | β-Cedrene | C15H24 |
| 27 | GERMACRENE D | C15H24 |
| 28 | α-Muurolene | C15H24 |
| 29 | γ-Cadinene | C15H24 |
| 30 | δ-Cadinene | C15H24 |
| 31 | α-Elemol | C15H26O |
| 32 | Cedrol | C15H26O |

TABLE 9-continued

| Peak | Compound name | Chemical formula |
|---|---|---|
| 33 | γ-Eudesmol | C15H26O |
| 34 | tau-Cadinol | C15H26O |
| 35 | tau-Muurolo* | C15H26O |

*similarity scores were less than 95% among data base.

Figure 13:
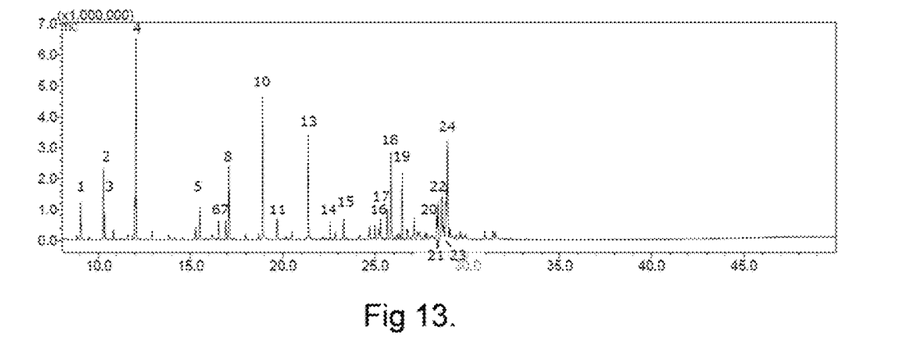
FIG. 13 is the analysis chart of the *Litsea cubeba* purification of the composition of the present invention, wherein the component less than 0.05% is not being labelled.

Please refer to Table 10 and FIG. 13, for chemical components contained in *Litsea cabeba*.

TABLE 10

| Peak | Compound name | Chemical formula |
|---|---|---|
| 1 | α-Pinene | C10H16 |
| 2 | Sabinene | C10H16 |
| 3 | β-Pinene | C10H16 |
| 4 | Cineole:Eucalyptol | C10H18O |
| 5 | Camphor | C10H16O |
| 6 | Terpinene-4-ol | C10H18O |
| 7 | α-Terpineol | C10H18O |
| 8 | Myrtenol | C10H16O |
| 9 | β-Citral | C10H16O |
| 10 | (−)-trans-Myrtanol | C10H18O |
| 11 | α-Citral | C10H16O |
| 12 | Safrole | C10H10O2 |
| 13 | α-Terpinyl acetate | C12H20O2 |
| 14 | β-Elemene | C15H24 |
| 15 | Caryophylene | C15H24 |
| 16 | α-Muurolene | C15H24 |
| 17 | γ-Cadinene | C15H24 |
| 18 | δ-Cadinene | C15H24 |
| 19 | α-Elemol | C15H26O |
| 20 | Cubenol* | C15H26O |
| 21 | γ-Eudesmol | C15H26O |
| 22 | tau-Cadinol | C15H26O |
| 23 | β-Eudesmol | C15H26O |
| 24 | tau-Muurolol* | C15H26O |

*similarity scores were less than 95% among data base.

Figure 14:
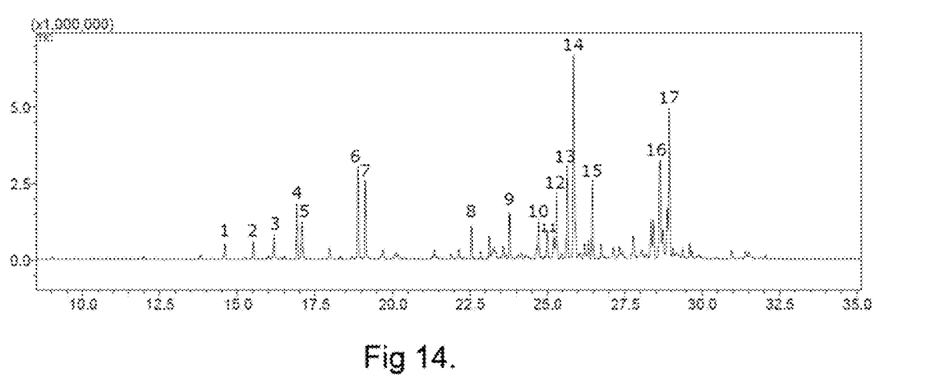
FIG. 14 is the analysis chart of the *Cinnamomum zeylanicum* purification of the composition of the present invention.

Please refer to Table 11 and FIG. 14, for chemical components contained in *Cinnamomum zeylanicum*.

TABLE 11

| Peak | Compound name | Chemical formula |
|---|---|---|
| 1 | (+)-Fenchol | C10H18O |
| 2 | Camphor | C10H16O |
| 3 | Borneol | C10H18O |
| 4 | α-Terpineol | C10HI18O |
| 5 | (−)-Myrtenol | C10H16O |
| 6 | (−)-trans-Myrtanol | C10H18O |
| 7 | Cinnamaldehyde | C10H16O |
| 8 | β-Elemene | C15H24 |
| 9 | Cinnamyl acetate | C11H12O2 |
| 10 | Cadinene isomer | C15H24 |
| 11 | β-Selinene | C25H24 |
| 12 | α-Muurolene | C15H24 |
| 13 | γ-Cadinene | C15H24 |
| 14 | δ-Cadinene | C15H24 |
| 15 | α-Elemol | C15H26O |
| 16 | tau-Cadinol | C15H26O |
| 17 | α-Cadinol | C15H26O |

Figure 15:
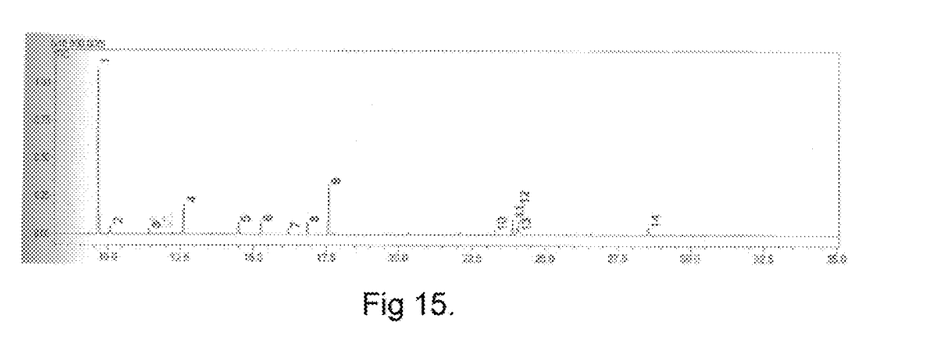
FIG. 15 is the analysis chart of the Taiwan *Cunninghamia lanceolatavar* purification of the composition of the present invention.

Please refer to Table 12 and FIG. 15, for chemical components contained in Taiwan *Cunninghamia lanceolata-var*.

TABLE 12

| Peak | Compound name |
|---|---|
| 1 | α-Pinene |
| 2 | Camphene |
| 3 | Myrcene |
| 4 | Limonene |
| 5 | α-Terpinolen |
| 6 | α-Fenchol |
| 7 | Camphor |
| 8 | Borneol |
| 9 | α-Terpineol |
| 10 | β-Elemene |
| 11 | α-Cedrene |
| 12 | Caryophyllene |
| 13 | β-Cedrene |
| 14 | Cedrol |

Figure 16:
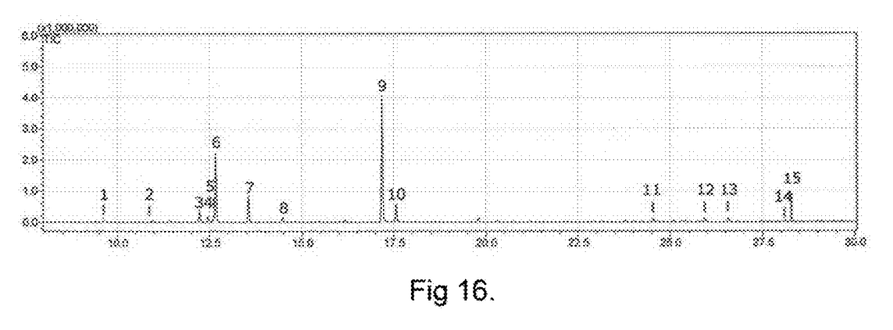
FIG. 16 is the analysis chart of the *Melaleuca alternifolia* purification of the composition of the present invention.

Please refer to Table 13 and FIG. 16, for chemical components contained in *Melaleuca alternifolia*.

TABLE 13

| Peak | Compound name | Chemical formula |
|---|---|---|
| 1 | α-Pinene | C10H16 |
| 2 | Sabinene | C10H16 |
| 3 | α-Terpinene | C10H16 |
| 4 | p-Cymene | C10H24 |
| 5 | Limonene | C10H16 |
| 6 | 1,8-Cineole | C10H18O |
| 7 | γ-Terpinene | C10H16 |
| 8 | Terpinolene | C10H16 |
| 9 | Terpinen-4-ol | C10H18O |
| 10 | α-Terpineol | C10H18O |
| 11 | Aromadendrene | C15H24 |
| 12 | Ledene | C15H24 |
| 13 | δ-Cadinene | C15H24 |
| 14 | Globulol | C15H26O |
| 15 | Viridiflorol | C15H26O |

Figure 17:
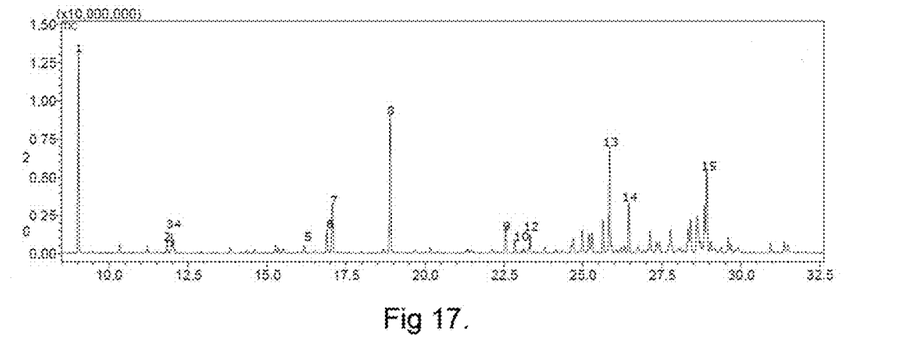
FIG. 17 is the analysis chart of the *Eucalyptus robusta* smith purification of the composition of the present invention, wherein the component less than 0.05% is not being labelled.

Please refer to Table 14 and FIG. 17, for chemical components contained in *Eucalyptus robusta* smith.

TABLE 14

| Peak | Compound name | Chemical formula |
|---|---|---|
| 1 | α-Pinene | C10H16 |
| 2 | p-Cymene | C10H14 |
| 3 | Limonene | C10H16 |
| 4 | Cineole | C10H18O |
| 5 | (−)-Borneol | C10H18O |
| 6 | α-Terpineol | C10H18O |
| 7 | (−)-Myrtenol | C10H16O |
| 8 | trans-Myrtanol | C10H18O |
| 9 | β-Elemene | C15H24 |
| 10 | β-Panasinsene | C15H24 |
| 11 | α-Cedrene | C15H24 |
| 12 | Caryophylene | C15H24 |
| 13 | δ-Cadinene | C15H24 |
| 14 | α-Elemol | C15H26O |
| 15 | α-Cadinol* | C15H26O |

*similarity scores were less than 95% among data base.

Figure 18:
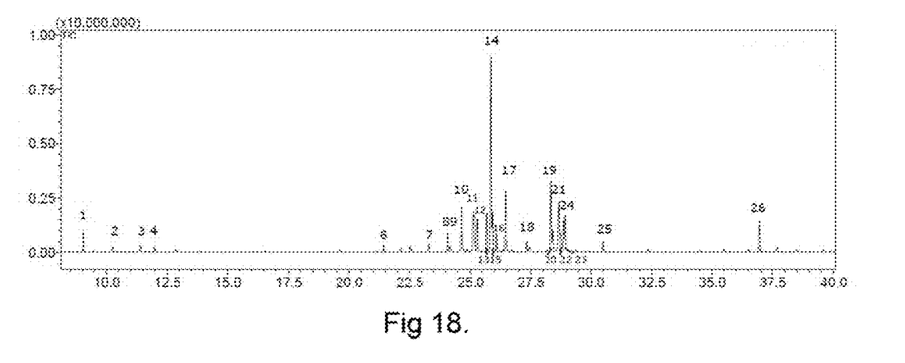
FIG. 18 is the analysis chart of the *Cryptomeria japonica* purification of the composition of the present invention, wherein the component less than 0.05% is not being labelled.

Please refer to Table 15 and FIG. 18, for chemical components contained in *Cryptomeria japonica*.

TABLE 15

| Peak | Compound name | Chemical formula |
| --- | --- | --- |
| 1 | α-Pinene | C10H16 |
| 2 | Sabinene | C10H16 |
| 3 | δ-3-Carene | C10H16 |
| 4 | Limonene | C10H16 |
| 5 | Cineole:Eucalyptol | C10H18O |
| 6 | α-Cubebene | C15H24 |
| 7 | Caryophyllene | C15H24 |
| 8 | N/A* | C15H24 |
| 9 | α-Humulene | C15H24 |
| 10 | N/A* | C15H24 |
| 11 | γ-Muurolene* | C15H24 |
| 12 | α-Muurolene | C15H24 |
| 13 | (−)-Cedreanol* | C15H26O |
| 14 | δ-Cadinene | C15H24 |
| 15 | (+)-Epizonarene | C15H24 |
| 16 | 4.10-dimethyl-7-isopropyl-bicyclo(4.4.0)-1,4-decadiene | C15H24 |
| 17 | α-Elemol | C15H26O |
| 18 | N/A* | C15H24 |
| 19 | N/A* | C15H24 |
| 20 | γ-Eudesmol | C15H26O |
| 21 | tau-Cadinol* | |
| 22 | δ-Cadinol | C15H26O |
| 23 | β-Eudesmol | C15H26O |
| 24 | 10-epi-γ-Eudesmol | C15H26O |
| 25 | N/A* | C15H24 |
| 26 | Kaur-16-ene | C20H32 |

*similarity scores were less than 95% among data base.

Figure 19:
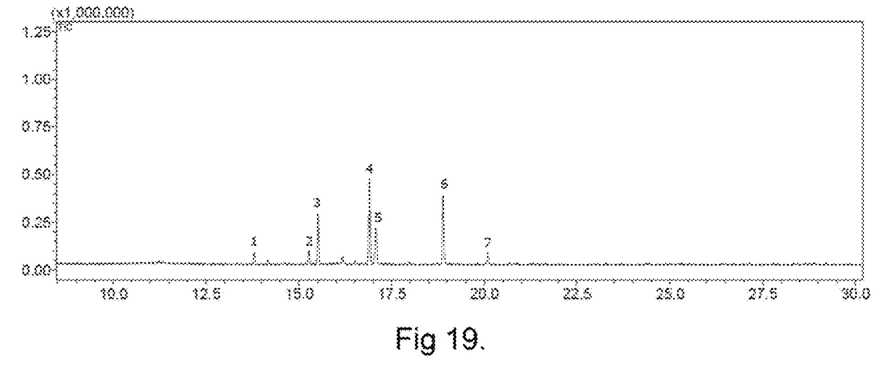
FIG. 19 is the analysis chart of the *Acacia confuse* purification of the composition of the present invention, wherein the component less than 0.05% is not being labelled.

Please refer to Table 16 and FIG. 19, for chemical components contained in *Acacia confuse*.

TABLE 16

| Peak | Compound name | Chemical formula |
| --- | --- | --- |
| 1 | L-Fenchone | C10H16O |
| 2 | (1R)-(+)-Norinone | C9H14O |
| 3 | Camphene | C10H16O |
| 4 | α-Terpineol | C10H18O |
| 5 | (−)-Myrtenol | C10H16O |
| 6 | (−)-cis-Myrtanol | C10H18O |
| 7 | cis-Terpin hydrate* | C10H20O2 |

*similarity scores were less than 95% among data base.

The aforementioned detailed illustrations are the specific explanations for the workable examples of the present invention. However, these examples are not used as a limitation to the scope of claims of the present invention. The equal application or modification which falls in the scope of the present invention is included in the scope of the present application.

What is claimed is:

1. A tumor cell-inhibiting composition, comprising 40% Taiwan cypress hydrosols, 10% stout camphor tree hydrosols, 10% Taiwan incense cedar hydrosols, 8% *Cinnamomum camphora* hydrosols, 8% *Cymbopogon nardus* hydrosols, 6% *Litsea cubeba* hydrosols, 6% *Cinnamomum zeylanicum* hydrosols, 4% *Cunninghamia lanceolata* hydrosols, 2% *Melaleuca alternifolia* hydrosols, 2% *Eucalyptus robusta* smith hydrosols, 2% *Cryptomeria japonica* hydrosols and 2% *Acacia confusa* hydrosols, wherein the hydrosols are obtained from a first stream of extracts of the plants by a kiln distillation method.

2. The tumor cell-inhibiting composition according to claim 1, wherein the composition inhibits the growth of the breast cancer cells.

3. The tumor cell-inhibiting composition according to claim 1, wherein the composition inhibits the growth of the hepatic carcinoma cells.

4. The tumor cell-inhibiting composition according to claim 1, wherein the composition inhibits the growth of the lung fibrous cells.

5. The tumor cell-inhibiting composition according to claim 1, wherein the composition comprises: 1,8-Cineole, Camphor, Borneol, Terpinen-4-ol, α-Terpineol, (−)-Myrtenol, cis-Myrtanol, α-Pinene, Camphene, Sabinene, Myrcene, 1,4-Cineole, α-Terpinene, Cymene, Limonene, γ-Terpinene, α-Terinolen, α-Fenchol, Citronellal, Citronellol, Nerol, Safrole, α-Terpinyl acetate, β-Elemene, α-Cedrene, β-Cedrene, α-Amorphene, β-Selinene, γ-2-Cadinene, α-Muurolene, γ-Cadinene, δ-Cadinene, β-Cadinene, α-Elemol, Cedrol, α-Cubebene, γ-Eudesmol, β-Eudesmol, tau-Muurolol.

\* \* \* \* \*